United States Patent

Blanchard et al.

[11] Patent Number: 5,540,845
[45] Date of Patent: Jul. 30, 1996

[54] METHOD OF AND APPARATUS FOR MONITORING AQUEOUS STREAMS

[75] Inventors: Michael J. Blanchard, Chesham; Brian Collins, Chalfont St. Giles, both of United Kingdom

[73] Assignee: Basil William Brook, Coventry, United Kingdom

[21] Appl. No.: 108,635

[22] PCT Filed: Feb. 26, 1992

[86] PCT No.: PCT/GB92/00347

§ 371 Date: Aug. 25, 1993

§ 102(e) Date: Aug. 25, 1993

[87] PCT Pub. No.: WO/9215873

PCT Pub. Date: Sep. 17, 1992

[30] Foreign Application Priority Data

Feb. 27, 1991 [GB] United Kingdom .................. 9104150
Mar. 11, 1991 [GB] United Kingdom .................. 9105103

[51] Int. Cl.⁶ .................................................... C02F 1/56
[52] U.S. Cl. .................. 210/709; 210/746; 210/96.1; 210/101; 324/71.1; 324/453
[58] Field of Search ................................ 210/709, 746, 210/96.1, 101; 324/71.1, 425, 453

[56] References Cited

U.S. PATENT DOCUMENTS

| 3,399,133 | 8/1968 | Gerdes et al. | 210/709 |
| 3,462,364 | 8/1969 | Carlson | 210/709 |
| 3,594,313 | 7/1971 | Carlson | 210/709 |
| 4,855,061 | 8/1989 | Martin | 210/746 |
| 5,202,016 | 4/1993 | Church et al. | 324/453 |
| 5,328,599 | 7/1994 | Siefert et al. | 210/101 |

FOREIGN PATENT DOCUMENTS

| 3344275 | 6/1985 | Germany | 210/709 |
| 404004100 | 1/1992 | Japan | 210/100 |
| 8806290 | 8/1988 | WIPO | |
| 9104486 | 4/1991 | WIPO | |

Primary Examiner—Peter A. Hruskoci
Attorney, Agent, or Firm—Michael J. Striker

[57] ABSTRACT

A metallic indicator electrode senses the anionic charge per unit time borne by the dispersed phase of a stream of an aqueous dispersion of negatively charged particles by virtue of the potential developed by the electrode as measured by a voltmeter. The developed potential can be used downstream, for example, to control the addition of a water treatment chemical or extraction of water from the stream.

6 Claims, 2 Drawing Sheets

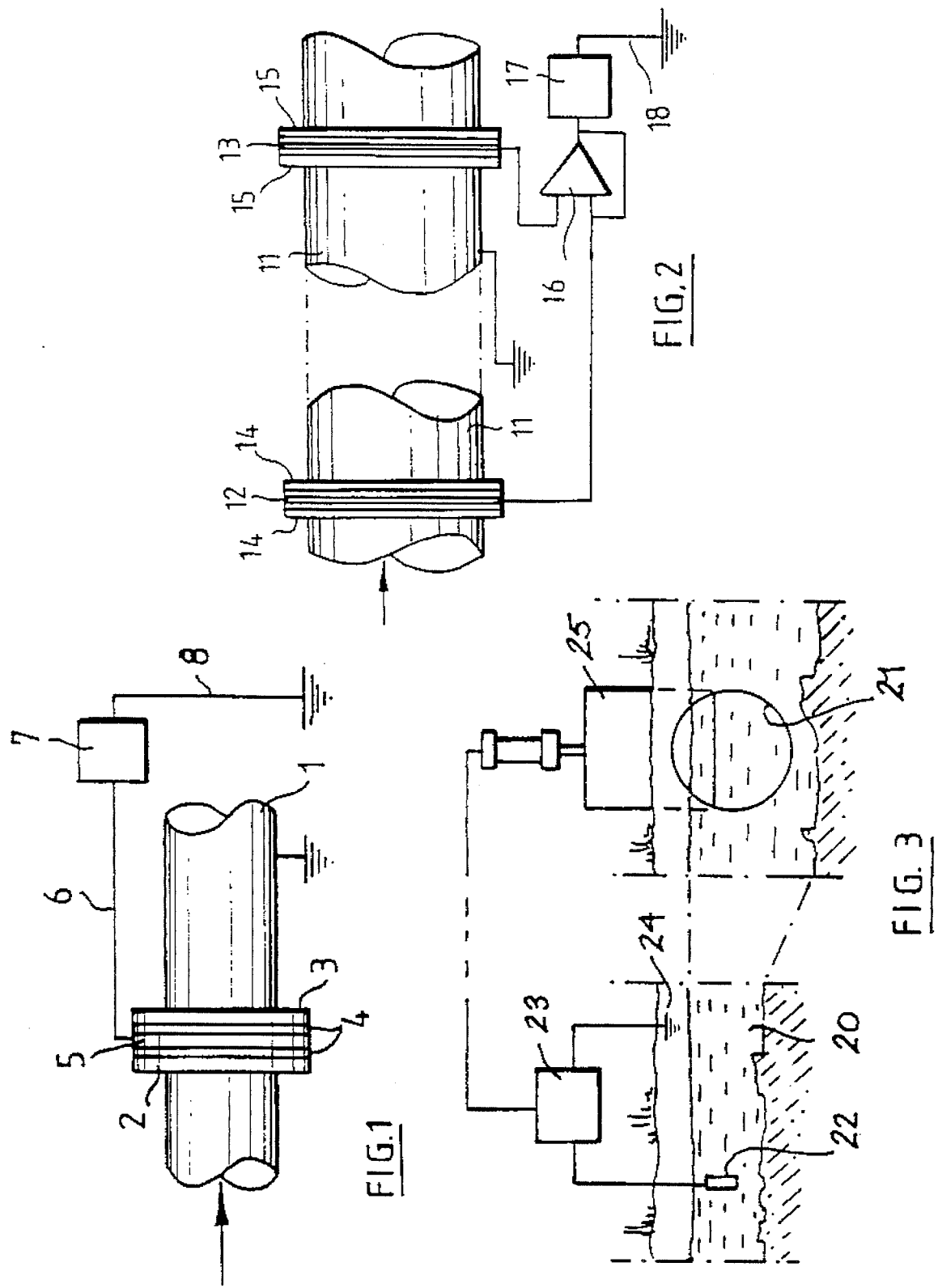

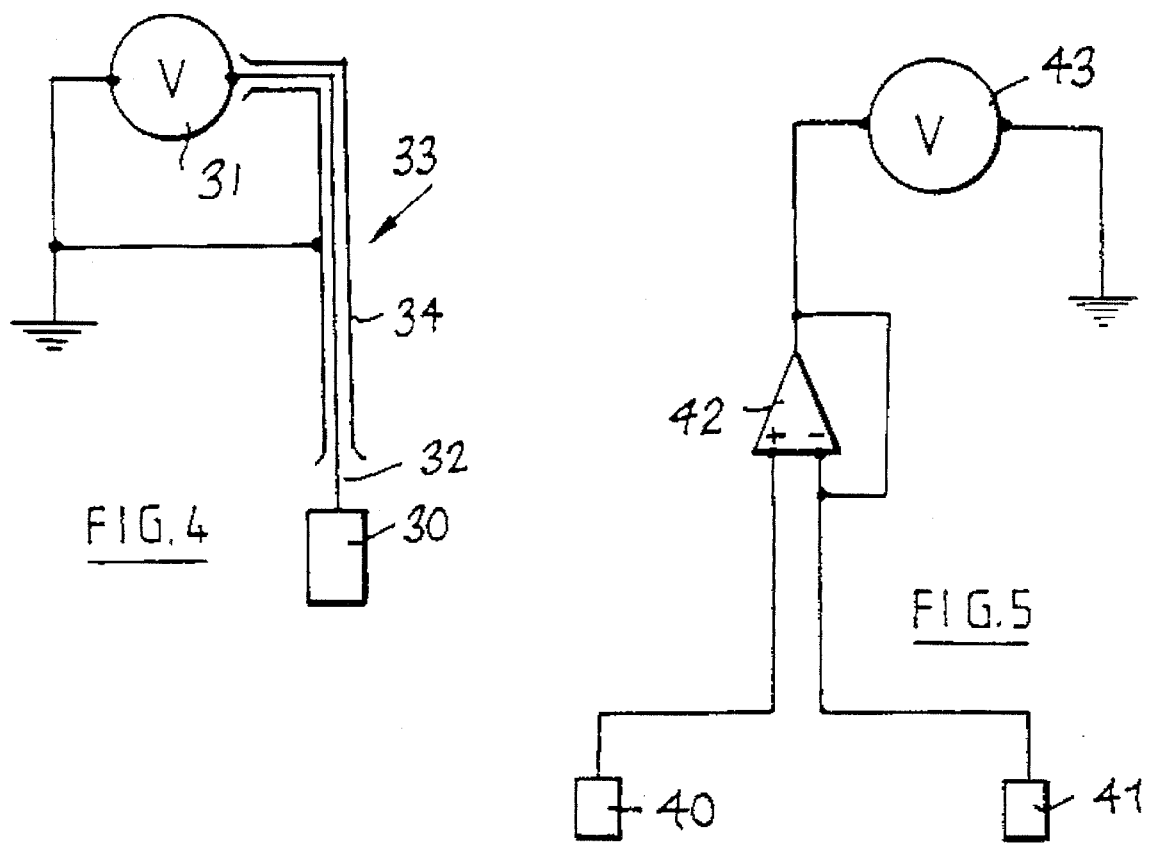
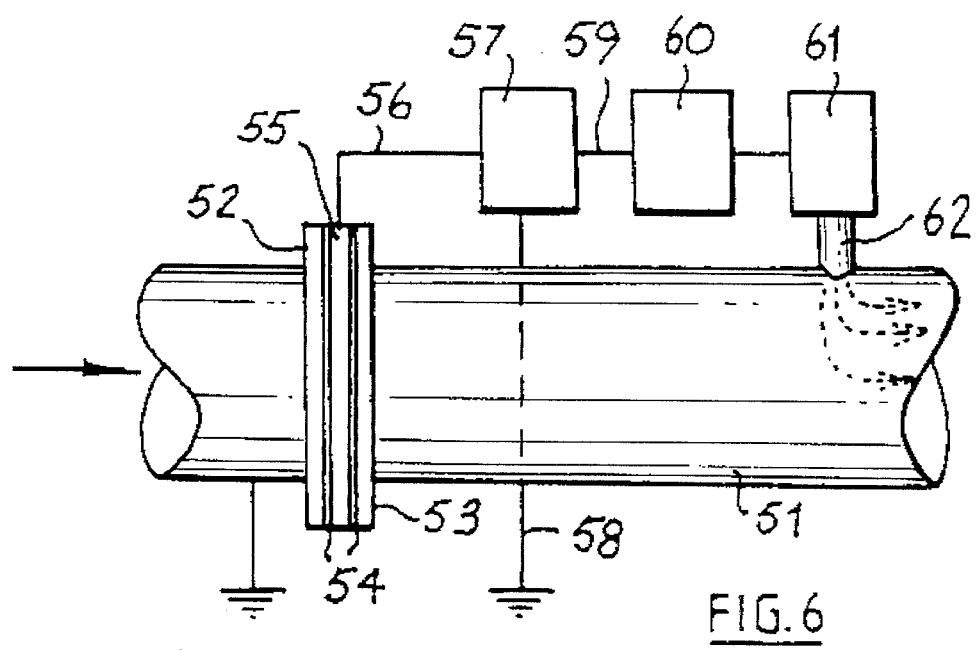

5,540,845

METHOD OF AND APPARATUS FOR MONITORING AQUEOUS STREAMS

TECHNICAL FIELD

This invention is concerned with a method of measuring the anionic charge content of an aqueous stream of an anionic dispersion, including identifying the incursion of an anionic dispersion into a less anionic aqueous stream.

1Field of the Invention

Anionic dispersions are commonplace: most natural dispersions—raw water sewage, sludges and effluents—and some man-made dispersions are anionic. Some are required whilst others are a nuisance or dangerous and need to be avoided or treated to remove the danger.

Many industries produce an aqueous stream which is ideally devoid of, or has at most a limited tolerance for, colloidally dispersed anionic solids or liquids. For example the product stream from a water treatment works, the effluent from an industrial or communal waste water works or the outfalls from farms, admitted to watercourses such as public waterways. Such a stream may be adventitiously polluted with colloidal suspended matter to the detriment of the quality of the stream.

Incidents have occurred where sludge has escaped from a sewage farm, or silage liquor or animal slurry from a farm, killing fish and leading people to doubt the quality of the water they use for recreation.

There is, therefore, a need for an instrument giving timely warning of such an incursion of a disperse phase of negatively charged particles into an aqueous stream.

2. Background of the Invention

The analysis of dispersions has hitherto been the province of electrokinetics which requires that the particles move relatively to the continuous phase. Either that movement is brought about by imposing an electric gradient on the dispersion via electrodes having an impressed potential difference, causing the dispersed particles to migrate towards the electrode of opposite potential (electrophoresis): or the particles are slowed relative to the fast flowing dispersion and the current generated by The mobile counterions swept from the surfaces of the dispersed phase, is collected on two electrodes as a potential difference or current (streaming potential or streaming current).

Electrophoresis is not applicable to opaque dispersions and Is probably only applied to stationary or slowly moving streams. Streaming potential or streaming current is not applicable to any stream with a substantial disperse phase-capillaries are essential elements of the apparatus and the dispersion must be able to pass through them. Hence electrokinetics is not suitable to analyse most everyday dispersions.

In the specification of WO91/04486 a device is described for sensing the course of the aggregation of an aqueous dispersion of charged particles in an aggregation control loop process. The device has a galvanic cell having a metallic indicator electrode without any particular ion-specificity and a second electrode, the electrolyte of the cell being a mixed stream of the dispersion and an aggregant for the charged particles and being in contact with the indicator electrode, and a means for sensing the potential difference appearing between the electrodes. This is an effective feedback control device which can be used in an aggregation control loop, for example, to control the addition of aggregant.

We have now discovered feed-forward (or feed-downstream) applications in which aggregant addition is not necessary upstream of the sensing-point so that it is not a mixed stream of aggregant and aqueous dispersion which is being charge-sensed. This invention allows the potential difference created in a galvanic cell where an aqueous stream of negatively charged particles is the electrolyte, to be used for pollution control.

SUMMARY OF THE INVENTION

According to one aspect of the present invention, a method of indicating changes in the anionic charge per unit time borne by the dispersed phase of a stream of an aqueous dispersion of negatively charged particles, comprises flowing the dispersion in contact with a first metallic indicator electrode, allowing the first indicator electrode to develop an electrical potential determined by the anionic charge per unit time of the stream flowing over the first indicator electrode, determining said developed electrical potential using a voltmeter bridging the first indicator electrode and a second electrode and using the potential difference recorded by the voltmeter as a measure of the anionic charge per unit time passing over the first indicator electrode.

The invention thus proposes applying potentiometry to measure the anionic charge content of anionic dispersions, a proposal for which there is no precedent.

The result is that any change in the anionic charge content, including incursions of a disperse phase, can be read as a change in the potential difference recorded by the voltmeter. Most natural dispersions are anionic and the potential difference becomes more negative with incursions of such dispersions. Connecting the voltmeter between the first indicator electrode (serving as a sensor electrode) and a second electrode (serving as a constant potential electrode) also dipping into the stream is a preferred arrangement, the constant potential of the second electrode being subtracted from the developed potential of the indicator electrode to give the potential measured by the voltmeter.

Hitherto, there was no theory which suggested that the arrival of a dispersed phase in a clear stream (or one already containing a constant concentration of a similarly charged dispersed phase) would vary the potential difference in a "galvanic" cell of which the "electrolyte" is the dispersion.

The indicator electrode spontaneously develops a potential difference between itself and the electrolyte with which it is in contact: the indicator electrode releases cations into the electrolyte in establishing an equilibrium potential and becomes negatively charged in the process. This potential, for a fixed temperature and pressure, is governed solely by the activity of the cations of the metallic indicator electrode dissolved in the electrolyte. The potential for a silver electrode, for example, is determined under constant external conditions, only by the activity of $Ag^+$ ions in solution.

Since the negatively-charged electrode is immersed in a stream which may become polluted with anionic dispersions, and since like charges repel, the negatively-charged solids in raw water or sludges are kept from settling on the indicator electrode.

The electrode potential developed by the first indicator electrode, because it is a measure of the chemical driving force of a half reaction, is affected by concentration. Thus the tendency of the metallic material of the indicator electrode to be oxidised to cations is substantially less in contact with a concentrated solution of the cation than it would be in contact with a dilute solution. Therefore the electrode potential for this process must also be less in a more concentrated solution.

When a dispersion is the "electrolyte", the anionic colloidal particles complex the cations released from the indicator electrode, rendering the electrolyte a more dilute solution of the cation and increasing the electrode potential. It is this interference with the concentration of solute ions by a solid disperse phase, which is the surprising contribution of the present invention. The indicator electrode functions as an electrode of the second order because its potential measures the concentration of a charged species (anionic colloidal particles) not directly involved in the electron-transfer process.

The first metallic electrode is preferably stainless steel (in one of its many varieties) since it is almost ideal in its resistance to the negatively charged particles encountered in raw water, polluted streams, municipal and industrial effluents, and its potential appears unaffected by any electrolytes in naturally occurring aqueous streams. However other metallic materials may be used for the indicator electrode.

The invention also includes in a further aspect, a method for identifying the incursion of an anionic colloidal dispersion into an aqueous stream, which comprises passing the aqueous stream in contact successively with a first and a second non-specific metal indicator electrode, and a common earthed electrode, measuring the potential difference between the indicator electrodes using an earthed voltmeter, and registering the incursion of a colloidal dispersion into the stream by noting a significant change in the potential difference measured.

In such a process, the potential difference between the indicator electrodes is registered by the voltmeter and will remain steady for so long as the quality of the stream remains constant between the two indicator electrodes, but when the stream is adulterated with a dispersion and comes into contact with either indicator electrode, the registered potential difference will change before the adulterated stream reaches the other indicator electrode to restore equilibrium conditions.

The components and properties of the aqueous stream which could affect the signal from the voltmeter if a lone indicator electrode were in use—temperature, salinity, oxygen content etc., are compensated for in using two indicator electrodes with similar responses to these variables and the easiest way of assuring this is to use indicator electrodes of similar material. This compensation is of particular importance for aqueous streams subject to seasonal and diurnal changes in ambient temperatures and rates of flow.

The indicator electrodes may be spaced apart along a pipeline, duct or stream and the incursion, when it occurs, will affect one (the upstream) electrode before the other, generating a change in the potential difference reading solely on the basis of the incoming colloid.

BRIEF DESCRIPTION OF THE DRAWINGS

The invention will now be further described, by way of example, with reference to the accompanying drawings, in which:

FIG. 1 is a schematic representation of a first embodiment of monitoring method, FIG. 2 is a schematic representation of a second embodiment of monitoring method, FIG. 3 is a schematic representation of a third embodiment of monitoring method, FIGS. 4 and 5 show useful electrode arrangements in the practice of the method of the invention, and FIG. 6 is a schematic representation of a fourth embodiment of monitoring method.

DESCRIPTION OF PREFERRED EMBODIMENTS

Referring to FIG. 1, an earthed metal pipe 1 (through which an aqueous sludge is flowing in the direction indicated by the arrow) incorporates a connection made up of flanges 2 and 3 on either side of electrically insulating gaskets 4 sandwiching an annular electrode 5 of stainless steel, the internal diameter of the annular electrode matching the internal diameter of the pipe. A screened cable 6 connects the electrode 5 to a voltmeter 7 the other terminal of which is connected to earth by a screened cable 8.

The reading of the voltmeter 7 varies in sympathy with the charge per unit time of the passing sludge. Thus as the negative charge per unit time on the particles in the flowing sludge increases (by a change in the nature of the particles, or an increase in the concentration of the particles, or an increase in the rate of flow of the sludge), the voltmeter signal will become less positive (the particles in all natural dispersions are negatively charged). Vice versa, the voltmeter signal becomes more positive as the charge per unit time of the flowing sludge decreases.

Referring to FIG. 2, an earthed metal pipe 11 carrying a stream of natural water has let in annular stainless steel indicator electrodes 12 and 13 set between pairs of insulating gaskets 14 and 15, respectively. A differential amplifier 16 is electrically connected to the two indicator electrodes, and a voltmeter 17 receives the output of the amplifier, the reference terminal 18 of the voltmeter being earthed.

The indicator electrodes 12 and 13 are set in the waterway above and below an outfall from a creamery to detect a seepage or flow of colloidal matter, the downstream electrode 13 acquiring a potential different from that of the upstream electrode 12 for the duration of the pollution from the creamery.

There is a class of galvanic cell recognised by electrochemists called "concentration cells": they measure the difference in the concentration of the cations released by two electrodes of similar metal, in two solutions as electrolytes. The apparatus described with reference to FIG. 2 is a sort of concentration cell in that it compares the concentration of ferrous ions from the stainless steel indicator electrodes. The anionic disperse phase complexes the ferrous ions in the neighbourhood of electrode 12, removing them from solution and reducing their concentration in the electrolyte, the reduced concentration producing an increased electrode potential compared with that of electrode 13.

The apparatus shown in FIGS. 1 and 2 may be augmented by an alarm circuit operable when a significant negative change in the potential difference between the indicator electrodes has appeared.

Fish farms and other operations which draw water from streams and rivers, may be protected from taking in muddy water or polluted water from a farm or creamery discharge, by locating an indicator electrode in the stream upstream of the intake. The following Example illustrates this.

EXAMPLE 1

A trout farm had four ponds containing the trout. The ponds were fed in sequence with water drawn, via a sluice-controlled intake 21, from a river 20 subject to significant changes in turbidity from rainstorms near its source (see FIG. 3), was equipped with a stainless steel electrode 22 connected via a voltmeter 23 to earth 24. The electrode was immersed in the river some 800 meters upstream of the intake 21 to the farm. The potential difference (PD) between the electrode 22 and the earth 24 on the river bank was registered on the voltmeter 23: when the river was of low turbidity, the potential difference was −234 millivolts, but following rain near the source of the river, the potential difference became more electronegative about 4 hours later.

It was found after several months of experience of various weather conditions, that water having a turbidity developing a potential difference of −272 millivolts was the most turbid water which could be tolerated as an intake to the farm. The alarm signal was set at −272 millivolts and the sluice controlling the intake was closed whenever the alarm was actuated. Since the installation (four months at the time of writing, including a rainy season), the farm has not suffered from taking in an unsuitable water, despite the turbidity of the flyer being sufficient to develop readings of −305 and −296 millivolts in isolated instances since the sluice gate 25 had been closed by an earlier warning before the unsuitable water reached the intake.

EXAMPLE 2

Farm silage liquor was added in various proportions to a clear river water and an indicator electrode 30 was connected to the positive terminal of a digital millivoltmeter 31 via the core 32 of a screened cable 33 (as shown in FIG. 4). The negative terminal of the voltmeter was connected to the grounded screen 34 of the cable 33. The electrode 30 was immersed in each mixture of water and liquor to produce the following potential difference readings:

| Nature of the water | PD measured |
| --- | --- |
| clear river water | −234 millivolts |
| clear river water + 0.5 parts per million silage liquor | −245 millivolts |
| clear river water + 1 part per million silage liquor | −255 millivolts |

EXAMPLE 3

At a farm having silage storage, a slurry pit and a silage liquor outfall into a river, two stainless steel electrodes 40 and 41 (see FIG. 5) were installed in the river, one upstream from the outfall and the other some 20 meters downstream from the outfall. The electrodes were connected via a differential amplifier 42 to one terminal of a voltmeter 43 the other terminal of which was connected to earth. The potential difference between the electrodes 40 and 41 appears on the voltmeter 43 and will be null when the quality of the water on contact with each of the electrodes is similar, but will have a different value if the water in contact with one electrode has a different anionic colloid content from that an contact with the other electrode With river water of substantially constant composition the potential difference arising between the electrodes was within a few millivolts of a null reading. The instrument was set to record events over a 48 hour interval. There occurred 5 periods each of from 1 to 3 hours duration when the potential difference reading was above −100 millivolts. Three of these readings were not correlated to the silage liquor content of the river, but of the two events which were observed, the seepage of silage liquor into the river was the obvious cause of the increase in electronegative reading occurring.

Referring to FIG. 6, items 51 to 58 are as identified in FIG. 1 with the addition of 50. Voltmeter 57 outputs its signal via a shrouded cable 59 to a controller 60 which deducts the potential characteristic of good quality coagulation and, after a delay corresponding to the time taken for the sludge to flow from the electrode 55 to a chemical dosing pump 61, relays the residual potential as a control signal to the pump 61 feeding branch pipe 62 downstream of the electrode 55. Thus the pump 61 is slowed or accelerated in accordance with the charge per unit time of the sludge adjacent the branch pipe. Such a "feed-forward" process has benefits compared to a feed-back system where there is a delay in the analysis and corrective action.

EXAMPLE 4

In a sewage treatment plant, a pipe conducted the sewage under constant flow conditions to a centrifuge. Flocculant was dosed to the sewage within the centrifuge by a pump equipped with both a speed control and a stroke control. The control of the dose was the duty of an operator who adjusted the stroke (leaving the speed unchanged) of the pump in accordance with the clarity of the water and the dryness of the solids discharged from the centrifuge. The plant records showed the average, minimum and maximum pump strokes in use over a period of six months.

The indicator electrode of an arrangement as shown in FIG. 6 was installed at the downstream end of the pipe in contact with the sewage immediately before it was discharged into the centrifuge. The sewage treatment was under good manual control. The controller 60 had a signal band width of from 4 to 20 milliamps and was calibrated to control the pump stroke to deliver the recorded minimum at 4 milliamps and the maximum recorded stroke at 20 milliamps with an intermediate datum signal of 12 milliamps corresponding to average stroke. The signal band width range was ramped to control the pump stroke to a value suiting the sewage under treatment. In this way the instrument automated what the operator did manually—fine tuning the demands for flocculant via control of the pump stroke—but with the advantage that the process was under continuous, uninterrupted control.

EXAMPLE 5

In a water treatment process, the speed of a coagulant dosing pump similar to the pump discussed in Example 4 was controlled by a flow meter monitoring the flow of treated water. This method of control takes no account of the ionic content of the raw water which the coagulant is to neutralise. An arrangement broadly according to FIG. 6 was installed with its indicator electrode immersed in slowly flowing raw water below a sluice gate controlling the intake to the plant. Once again the average, minimum and maximum pump strokes were available from records; the extremes of the band width of from 4 to 20 milliamps were calibrated as the minimum and maximum strokes respectively with the average stroke associated with 12 milliamps. The arrangement was then put in control of the stroke of the pump and the treatment continued satisfactory for the duration of a two week trial without human intervention.

We claim:

1. A method for controlling dosing of water treatment chemical from a pump having an outlet, the method comprising the steps of sensing a concentration of negatively charged particles in a stream of water at a point upstream of the pump outlet, said sensing including the steps of flowing said water and charged particles as a dispersion in contact with a first metallic indicator electrode; allowing the first indicator electrode to develop an electrical potential determined by an anionic charge per unit time of the stream of dispersion flowing over the first indicator electrode, determining said developed electrical potential using a voltmeter bridging the first indicator electrode and a second electrode; using a potential difference recorded by the voltmeter as a measure of the anionic charge per unit time passing over the first indicator electrode; and controlling operation of the pump on the basis of the thusly sensed concentration and the time for the stream to flow from the indicator electrode to the pump outlet.

2. An apparatus for controlling the addition of water treatment chemicals downstream of an indicator electrode sensing a concentration of anionic particles in a flowing aqueous stream, the apparatus comprising a first metallic indicator electrode arranged so that an aqueous dispersion of negatively charged particles flows in contact with said first metallic indicator electrode allowing said first indicator electrode to develop an electrical potential determined by the anionic charge per unit time of the stream flowing over said first indicator electrode; a second electrode; a voltmeter bridging said first indicator electrode and said second electrode and determining the developed electrical potential therebetween so as to use a potential difference determined by said voltmeter as a measure of the anionic charge per unit time passing over said first indicator electrode; and means for controlling the addition of said water treatment chemicals downstream of said indicator electrode based on the concentration of anionic particles sensed in the flowing aqueous stream by the voltmeter and the flow time between said indicator electrode and said means for controlling.

3. Apparatus as defined in claim 2, wherein the second electrode is a grounded electrode.

4. A method of indicating changes in an anionic charge per unit time borne by a dispersed phase of a stream of an aqueous dispersion of negatively charged particles flowing through an intake of a pollution-sensitive plant, the method comprising the steps of flowing the dispersion in contact with a first metallic indicator electrode located upstream of said intake; allowing the first indicator electrode to develop an electrical potential determined by the anionic charge per unit time of the stream flowing over the first indicator electrode; determining said developed electrical potential using a voltmeter bridging the first indicator electrode and a second electrode; using a potential difference recorded by the voltmeter as a measure of the anionic charge per unit time passing over the first indicator electrode, wherein the pollution of said aqueous stream approaching said intake of said pollution-sensitive plant is represented by indicated changes in measured anionic charge; recording a change in the potential difference sensed by the voltmeter; and using the recorded change to close off the intake and prevent flow of a polluted aqueous stream through said intake.

5. A method of indicating changes in an anionic charge per unit time borne by a dispersed phase of a stream of an aqueous dispersion of negatively charged particles, the method comprising the steps of flowing the dispersion in contact with a first metallic indicator electrode; allowing the first indicator electrode to develop an electrical potential determined by the anionic charge per unit time of the stream flowing over the first indicator electrode; determining said developed electrical potential using a voltmeter bridging the first indicator electrode and a second electrode; using a potential difference recorded by the voltmeter as a measure of the anionic charge per unit time passing over the first indicator electrode; and limiting pollution in said stream by titrating one of a coagulant and a flocculant for polluting negatively charged particles into the stream downstream of the indicator electrode at a rate dictated by the potential difference recorded.

6. A method as defined in claim 5, wherein said titrating includes titrating by a pump having a pumping rate, said pumping rate being slowed or accelerated in accordance with the charge per unit time monitored by the indicator electrode.

* * * * *